(12) United States Patent
Hess et al.

(10) Patent No.: US 8,361,800 B2
(45) Date of Patent: Jan. 29, 2013

(54) DIAGNOSTIC MEANS AND METHODS USING TROPONIN T AND NT-PROBNP

(75) Inventors: Georg Hess, Mainz (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/465,825

(22) Filed: May 14, 2009

(65) Prior Publication Data

US 2010/0075429 A1  Mar. 25, 2010

Related U.S. Application Data

(63) Continuation of application No. PCT/EP2007/062562, filed on Nov. 20, 2007.

(30) Foreign Application Priority Data

Nov. 21, 2006 (EP) .................................. 06124479
Feb. 8, 2007 (EP) .................................. 07101946

(51) Int. Cl.
    *G01N 33/00* (2006.01)
(52) U.S. Cl. .............................. 436/86; 436/811; 435/7.1
(58) Field of Classification Search .................... 436/86, 436/811; 435/7.1
    See application file for complete search history.

(56) References Cited

U.S. PATENT DOCUMENTS

| | | | |
|---|---|---|---|
| 5,744,305 A | 4/1998 | Fodor et al. | |
| RE39,816 E * | 9/2007 | Stanton et al. | 435/7.92 |
| 7,632,647 B2 * | 12/2009 | Dahlen et al. | 435/7.1 |
| 2004/0121343 A1 * | 6/2004 | Buechler et al. | 435/6 |
| 2004/0171064 A1 * | 9/2004 | Dahlen et al. | 435/7.1 |
| 2006/0183681 A1 | 8/2006 | Ebrahim et al. | |
| 2006/0234304 A1 * | 10/2006 | Amann-Zalan et al. | 435/7.1 |

FOREIGN PATENT DOCUMENTS

| | | |
|---|---|---|
| EP | 0648228 B1 | 11/1998 |
| EP | 1890153 A1 | 2/2008 |
| WO | 02/083913 A1 | 10/2002 |
| WO | 02/089657 A3 | 11/2002 |
| WO | 2004/045381 A2 | 6/2004 |

OTHER PUBLICATIONS

Goto et al. "Circulating concentrations of cardiac proteins indicate severity of congestive heart failure", Heart, 89, 1303-1307 (2003).*
Morrow et al. "Future Biomarkers in Acute Coronary Syndromes: Moving Toward a Multimarker Strategy", Circulation, 108, 250-252 (2003).*

(Continued)

*Primary Examiner* — Jill Warden
*Assistant Examiner* — Monique Cole
(74) *Attorney, Agent, or Firm* — Roche Diagnostics Operations, Inc.

(57) ABSTRACT

The present invention relates to diagnostic means and methods. Specifically, the present invention encompasses a method of diagnosing the cause of cardiac necrosis in a subject comprising determining the amount of a cardiac troponin and the amount of a BNP-type peptide in a sample from a subject suffering from cardiac necrosis and comparing the amount of the cardiac troponin and the amount of the BNP-type peptide to reference amounts, whereby the cause of the cardiac necrosis is to be diagnosed. The present invention further relates to a method of determining whether a subject suffering from cardiac necrosis is susceptible for a therapy against initial heart failure and to a method for determining whether a subject suffering from cardiac necrosis is susceptible for a therapy against coronary heart disease. Also encompassed are diagnostic uses, devices, and kits.

21 Claims, 4 Drawing Sheets

OTHER PUBLICATIONS

International Search Report issued May 15, 2008 in PCT Application No. PCT/EP2007/062562.

International Preliminary Report on Patentability issued Mar. 9, 2009 in PCT Application No. PCT/EP2007/062562.

Anderson, Page A. W. et al., Molecular Basis of Human Cardiac Troponin T Isoforms Expressed in the Developing, Adult, and Failing Heart, Circulation Research, 1995, pp. 681-686, vol. 76, No. 4.

Bonow, Robert O., New Insights Into the Cardiac Natriuretic Peptides, Circulation, 1996, pp. 1946-1950, vol. 93.

Bristow, Michael R. and Lowes, Brian D., Braunwald's Heart Disease a Textbook of Cardiovascular Medicine 7th Edition, 2005, Chapter 24 Management of Heart Failure, Figs 24G-1 to 24G-7, pp. 618-623, Elsevier's Health Sciences, Philadelphia, PA.

Camici, Paolo G. and Crea, Filippo, Coronary Microvascular Dysfunction, The New England Journal of Medicine, 2007, pp. 830-840, vol. 356.

De Lemos, James et al., Combining natriuretic peptides and necrosis markers in the assessment of acute coronary syndromes, Reviews in Cardiovascular Medicine, 2003, pp. S37-S46, vol. 4, Supplement 4.

Ferrieres, Gaelle et al., Human cardiac troponin I: precise identification of antigenic epitopes and prediction of secondary structure, Clinical Chemistry, 1998, pp. 487-493, vol. 44, No. 3.

Fonarow, Gregg C. and Horwich, Tamara B., Combining Natriuretic Peptides and Necrosis Markers in Determining Prognosis in Heart Failure, Reviews in Cardiovascular Medicine, 2003, pp. S20-S28, vol. 4, Supplement 4.

Gheorghiade, Mikhai et al., Navigating the Crossroads of Coronary Artery Disease and Heart Failure, Circulation, 2006, pp. 1202-1213, vol. 114.

Hours, S. et al., Value and interest of biological cardiac markers (BNP and troponin) in intensive care unit, Réanimation, 2004, pp. 112-119, vol. 13, No. 2.

Karl, J. et al., Development of a novel, N-Terminal-proBNP (NT-proBNP) assay with a low detection limit, Scandinavian Journal of Clinical Laboratory Investigation, 1999, pp. 177-181, vol. 59, Supplement 230.

Koh, Eikan et al., Troponin-T and Brain Natriuretic Peptide as Predictors for Adriamycin-Induced Cardiomyopathy in Rats, Circulation Journal, Feb. 2004, pp. 163-167, vol. 68, No. 2.

Krzeminska-Pakula, M., Biomarkers in acute coronary syndromes in women. Helpful for risk stratification and therapeutic decision making?, Polski Przeglad Kardiologiczny, 2006, pp. 41-44, vol. 8, No. 1.

Maron, Barry J. et al., Contemporary Definitions and Classification of the Cardiomyopathies: An American Heart Association Scientific Statement From the Council on Clinical Cardiology, Heart Failure and Transplantation Committee; Qualify of Care and Outcomes Research and Functional Genomics and Translational Biology Interdisciplinary Working Groups; and Council on Epidemiology and Prevention, Circulation, 2006, pp. 1807-1816, vol. 113.

Mueller, Thomas et al., Long-term stability of endogenous B-type natriuretic peptide (BNP) and amino terminal proBNP (NT-proBNP) in frozen plasma samples, Clin Chem Lab Med, 2004, pp. 942-944, vol. 42, No. 8.

Nolan, John P. and Sklar, Larry A., Suspension array technology: evolution of the flat-array paradigm, Trends in Biotechnology, Jan. 2002, pp. 9-12, vol. 20, No. 1.

Ravkilde, Jan, Risk stratification of acute coronary syndrome patients. A multi-marker approach, Scandinavian Journal of Clinical and Laboratory Investigation, 2005, pp. 25-29, vol. 65, No. Supplement 240.

Smith, M. W. et al., Delayed metabolism of human brain natriuretic peptide reflects resistance to neutral endopeptidase, Journal of Endocrinology, 2000, pp. 239-246, vol. 167.

Taniguchi, Ryoji et al., Combined Measurements of Cardiac Troponin T and N-Terminal Pro-Brain Natriuretic Peptide in Patients With Heart Failure, Circulation Journal, Dec. 2004, pp. 1160-1164, vol. 68, No. 12.

Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.

Yeo, Kiang-Teck J. et al., Multicenter evaluation of the Roche NT-proBNP assay and comparison to the Biosite Triage BNP assay, Clinica Chimica Acta, 2003, pp. 107-115, vol. 338.

Horwich, Tamara B. et al., "Cardiac Troponin I Is Associated With Impaired Hemodynamics, Progressive Left Ventricular Dysfunction, and Increased Mortality Rates in Advanced Heart Failure," Circulation, 2003, pp. 833-838, vol. 108.

Ishii, Junnichi et al., "Risk Stratification Using a Combination of Cardiac Troponin T and Brain Natriuretic Peptide in Patients Hospitalized for Worsening Chronic Heart Failure," The American Journal of Cardiology, 2002, pp. 691-695, vol. 89.

James, Stefan K. et al., "Troponin-T and N-Terminal Pro-B-Type Natriuretic Peptide Predict Mortality Benefit From Coronary Revascularization in Acute Coronary Syndromes A Gusto-IV Substudy," Journal of the American College of Cardiology, 2006, pp. 1146-1154, vol. 48, No. 6.

Jelic, Sanja and Le Jemtel, Thierry H., "Diagnostic Usefulness of B-Type Natriuretic Peptide and Functional Consequences of Muscle Alterations in COPD and Chronic Heart Failure," Chest, 2006, pp. 1220-1230, vol. 130.

Korff, Susanne et al., "Differential Diagnosis of Elevated Troponins," Heart, 2006, pp. 987-993, vol. 92.

See, Raphael and De Lemos, James A., "Current Status of Risk Stratification Methods in Acute Coronary Syndromes," Current Cardiology Reports, 2006, pp. 282-288, vol. 8.

Weber, Michael and Hamm, Christian, "Role of B-Type Natriuretic Peptide (BNP) and NT-PROBNP in Clinical Routine," Heart, 2006, pp. 843-849, vol. 92.

\* cited by examiner

DIAGNOSTIC MEANS AND METHODS USING TROPONIN T AND NT-PROBNP

RELATED APPLICATIONS

This application is a continuation of PCT/EP2007/062562 filed Nov. 20, 2007 and claims priority to EP 07101946.7 filed Feb. 8, 2007 and to EP 06124479.4 filed Nov. 21, 2006.

FIELD OF THE INVENTION

The present invention relates to diagnostic means and methods. Specifically, the present invention encompasses a method of diagnosing the cause of cardiac necrosis in a subject comprising determining the amount of a cardiac troponin and the amount of a BNP-type peptide in a sample from a subject suffering from cardiac necrosis and comparing the amount of the cardiac troponin and the amount of the BNP-type peptide to reference amounts, whereby the cause of the cardiac necrosis is to be diagnosed. The present invention further relates to a method of determining whether a subject suffering from cardiac necrosis is susceptible for a therapy against initial heart failure and to a method for determining whether a subject suffering from cardiac necrosis is susceptible for a therapy against coronary heart disease. Also encompassed are diagnostic uses, devices, and kits.

BACKGROUND

An aim of modern medicine is to provide personalized or individualized treatment regimens. Those are treatment regimens which take into account a patient's individual needs or risks. Personalized or individual treatment regimens shall be even taken into account for emergency measures where it is required to decide on potential treatment regimens within short periods of time. Heart diseases are the leading cause of morbidity and mortality in the Western hemisphere. The diseases can remain asymptomatic for long periods of time. However, they may have severe consequences once an acute cardiovascular event, such as myocardial infarction, as a cause of the cardiovascular disease occurs.

In particular, cardiac necrosis is a disease or disorder of the myocardium which severely affects the function of the heart and which often results in life-threatening myocardial infarction or progression of heart failure (i.e. the so called progressive heart failure). Cardiac necrosis may have diverse causes and, therefore, may require different treatment regimens depending on the cause.

The causes of cardiac necrosis include heart failure as well as coronary heart diseases as well as cardiac myopathy. It is to be understood that as different the causes are as different are the therapies which can be applied. Specifically, in the case of heart failure a drug based therapy may appear promising while for a coronary heart disease, such as a stenosis of a coronary artery, an invasive therapy will be necessary, e.g., an angioplasty or bypass surgery (for details see Gheorghiade 2006, Circulation 114:1202-1213).

The conventional diagnostic techniques for cardiac necrosis include pivotally electrocardiographic measurements. Recently, these conventional techniques have been further strengthened by the analysis of cardiac troponin I or troponin T as biomarkers. These diagnostic techniques, however, do not allow determining the cause of a cardiac necrosis without further differential diagnosis. Thus, various different diagnostic measures have to be carried out subsequently in order to determine the cause of cardiac necrosis. However, in cases where such a time consuming diagnostic procedure is impossible or expensive, e.g., for emergency patients, a personalized treatment regimen can not be determined with sufficient accuracy. As a consequence thereof, many patients will receive a treatment regimen which is insufficient or which may have adverse side effects.

Therefore, there is a need for diagnostic or prognostic measures which allow a reliable and fast diagnosis of the cause of a cardiac necrosis in order to determine suitable treatment regimens.

The technical problem underlying the present invention can be seen as the provision of means and methods for complying with the aforementioned needs. The technical problem is solved by the embodiments characterized in the claims and herein below.

SUMMARY OF THE INVENTION

The present invention, thus, relates to a method of diagnosing the cause of cardiac necrosis in a subject comprising:
  (a) determining the amount of a cardiac troponin and the amount of a BNP-type peptide in a sample of subject suffering from cardiac necrosis; and
  (b) comparing the amount of the cardiac troponin and the amount of the BNP-type peptide to reference amounts, whereby the cause of the cardiac necrosis is to be diagnosed.

DETAILED DESCRIPTION OF THE INVENTION

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification of a subject in need of a cardiac intervention. The method may be carried out manually or assisted by automation. Preferably, step (a) and/or (b) may in total or in part be assisted by automation, e.g., by a suitable robotic and sensory equipment for the determination in step (a) or a computer-implemented comparison in step (b).

The term "diagnosing" as used herein means identifying the cause of the cardiac necrosis, i.e. the underlying disorder or disease condition resulting in the apparent cardiac necrosis. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

Diagnosing according to the present invention includes monitoring, confirmation, subclassification and prediction of the relevant disease, symptoms or risks therefor. Monitoring relates to keeping track of an already diagnosed disease. Confirmation relates to the strengthening or substantiating a diagnosis already performed using other indicators or markers. Subclassification relates to further defining a diagnosis according to different subclasses of the diagnosed disease, e.g. defining according to mild and severe forms of the disease.

The term "cardiac necrosis" as used herein refers to necrotic cells or tissue of the myocardium. Such necrotic cells or tissue areas can be determined electrocardiographic techniques because the necrotic cells or areas shall influence the electric field produced by a physiologically operating, i.e. beating, heart. Low blood pressure, elevated intraventricular pressure or coronary heart diseases as well as cardiac myopathy are well known disorders which result in a reduced perfusion of the myocardium and, consequently, in cardiac necrosis. A cardiac myopathy in accordance with the present invention relates to a disorder affecting the myocardium accompanied by mechanical or electrophysiological alterations. Moreover, the disorder may be accompanied by hypertrophia or dilatation of the heart ventricles. Cardiac myopathy may result, e.g., from inflammatory diseases of the myocardium or may be caused by toxic compounds (see also Maron 2006, Circulation 113:1807-1816). It is well established that cardiac necrosis is accompanied by worsening of the function of the heart. This disorder is also called progressive heart failure and shall result in an ischemic cardiac myopathy. Accordingly, it is to be understood that the method of the present invention can be also applied to diagnose the cause of ischemic cardiac myopathy, e.g. as a result of a progressive heart failure or coronary heart disease.

The causes of cardiac necrosis and, thus, progressive heart failure are either a coronary heart disease resulting in a reduced blood flow throughout the coronary vessels and consequently to hypoxic or ischemic areas in the myocardium. On the other hand, hypoxia or ischemia of the myocardium and, thus, cardiac necrosis accompanied by a progressive heart failure may also result from an initial heart failure. An initial heart failure as referred to herein, preferably, results from either elevated intraventricular pressure, low blood pressure or a dilatative cardiac myopathy.

Ischemia which may be responsible for the cardiac necrosis referred to herein may be a reversible or persisting (i.e. permanent) ischemia. Persisting ischemia is characterized in that the myocardium is inappropriately supplied by blood and, thus, hypoxic, even in a resting subject, i.e. not applied to physical or pharmacological stress, e.g., bicycle exercise or dipyridamol. The reversible ischemia is characterized in that the inappropriate blood supply of the myocardium occurs only upon application of physical or pharmacological stress. As set forth above already, cardiac necrosis may be also the result of other causes and, thus, is not necessarily accompanied by ischemia.

The term "coronary heart diseases" as used herein encompass coronary artery diseases including stenosis, atherosclerosis of the coronary vessels or occlusions, such as thromboembolic occlusions within the coronary vessel system.

The term "subject" as used herein relates to animals, preferably mammals, and, more preferably, humans. Preferably, the subject referred to in accordance with the aforementioned method suffers from a cardiac necrosis or exhibits the symptoms accompanied therewith, i.e. being at least suspect to suffer from cardiac necrosis.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac troponin refers to troponin T and/or troponin I, and, most preferably, to troponin T. It is to be understood that isoforms of troponins may be determined in the method of the present invention together, i.e. simultaneously or sequentially, or individually, i.e. without determining the other isoform at all. Amino acid sequences for human troponin T and human troponin I are disclosed in Anderson, loc cit and Ferrieres 1998, Clinical Chemistry, 44: 487-493.

The term "cardiac troponin" encompasses also variants of the aforementioned specific troponins, i.e., preferably, of troponin T or troponin I. Such variants have at least the same essential biological and immunological properties as the specific cardiac troponins. In particular, they share the same essential biological and immunological properties if they are detectable by the same specific assays referred to in this specification, e.g., by ELISA Assays using polyclonal or monoclonal antibodies specifically recognizing the cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins. Further included are variants which differ due to posttranslational modifications such as phosphorylation or myristylation.

The term "brain natriuretic peptide (BNP)-type peptides" relates to pre-proBNP, proBNP, NT-proBNP, and BNP and variants thereof having the same predictive potential (see e.g. Bonow, 1996, Circulation 93: 1946-1950). Specifically, the aforementioned pre-pro peptide of the brain natriuretic peptide (having 134 amino acids in length) comprises a short signal peptide, which is enzymatically cleaved off to release the pro peptide (108 amino acids). The pro peptide is further cleaved into an N-terminal pro peptide (NT-pro peptide, 76 amino acids) and the active hormone (32 amino acids).

BNP is metabolised in the blood, whereas NT-proBNP circulates in the blood as an intact molecule and as such is eliminated renally. The in-vivo half-life of NTproBNP is 120 min longer than that of BNP, which is 20 min (Smith 2000, J Endocrinol. 167: 239-46). Preanalytics are more robust with NT-proBNP allowing easy transportation of the sample to a central laboratory (Mueller 2004, Clin Chem Lab Med 42: 942-4). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73). Therefore, depending on the time-course or properties of interest, either measurement of the active or the inactive forms of the BNP-type peptides can be advantageous.

The most preferred BNP-type peptide referred to herein is human NT-proBNP. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Invest 59:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

Determining the amount of the peptides or polypeptides referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on ELECSYS analyzers, Roche Diagnostics GmbH), CBA (an enzymatic cobalt binding assay, available for example on Roche-Hitachi analyzers), and latex agglutination assays (available for example on Roche-Hitachi analyzers).

Preferably, determining the amount of a peptide or polypeptide comprises the steps of (a) contacting a cell capable of eliciting a cellular response the intensity of which is indicative of the amount of the peptide or polypeptide with the peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxigenin, His-Tag, Glutathione-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568): Further fluorescent labels are available e.g. from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g. a light-sensitive film or a phosphor imager. Suitable measurement methods according the present invention also include precipitation (particularly immunoprecipitation), electro-chemiluminescence (electro-generated chemiluminescence), RIA (radioimmunoassay), ELISA (enzyme-linked immunosorbent assay), sandwich enzyme immune tests, electro-chemiluminescence sandwich immunoassays (ECLIA), dissociation-enhanced lanthanide fluoroimmuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the polypeptide or peptide as well as any value or parameter which correlates thereto or can be derived therefrom. Such values or parameters comprise intensity signal values from all specific physical or chemical properties obtained from the peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount determined in step a) and the reference amount, it is possible to identify the cause of a cardiac necrosis. Therefore, the reference amount is to be chosen so that either a difference or a similarity in the compared amounts allows identifying those subjects which belong into the group of subjects suffering from a cardiac necrosis either caused by initial heart failure or by a coronary heart disease.

Accordingly, the term "reference amounts" as used herein refers to amounts of the polypeptides which allow identifying a subject suffering from a cardiac necrosis either caused by initial heart failure or by a coronary hart disease. Accordingly, the reference may either be derived from (i) a subject known to suffer from a cardiac necrosis caused by initial heart failure or (ii) a subject known to suffer from a cardiac necrosis caused by a coronary heart disease. Moreover, the reference amounts, preferably, define thresholds. Suitable reference amounts or threshold amounts may be determined by the method of the present invention from a reference sample to be analyzed together, i.e. simultaneously or subsequently, with the test sample. A preferred reference amount serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques. A suitable technique may be to determine the median of the population for the peptide or polypeptide amounts to be determined in the method of the present invention. The ULN for a cardiac troponin and, in particular, for troponin T referred to herein, preferably, varies between 0.001 ng/ml and 0.01 ng/ml. More preferably, the ULN for the cardiac troponin is 0.001 ng/ml. The ULN for a BNP-type peptide and, in particular, for NT-proBNP referred to herein, preferably, varies between 100 and 150 pg/ml. More preferably, the ULN for the BNP-type peptide is 125 pg/ml.

In principle, it has been found that increased amounts of a BNP-type peptide in combination with increased amounts of a cardiac troponin in a sample of a subject are indicative for a cardiac necrosis caused by initial heart failure while increased amounts of a cardiac troponin in the absence of increased amounts of a BNP-type peptide are indicative for a coronary heart disease as a cause of the cardiac necrosis. Based on said findings, the cause of cardiac necrosis can be determined by the method of the present invention.

Advantageously, it has been found in the study underlying the present invention that a combination of a cardiac troponin such as troponin T and a BNP-type peptide such as NT-proBNP as biomarkers are sufficient to resolve the cause of cardiac necrosis in a reliable and efficient manner. As described above, the techniques which are currently used to resolve the cause of cardiac necrosis are both time consuming and cost intensive. Moreover, the techniques can usually not be implemented in portable systems. The method of the present invention, however, allows a reliable, fast and less cost intensive diagnosis and can be implemented even in portable assays, such as test strips. Therefore, the method is particularly well suited for diagnosing emergency patients. Further, the method of the present invention is to be carried out on a sample of a subject and, therefore, has a drastically reduced risk of causing adverse side effects which can not be avoided at least for the invasive prior art techniques. Thanks to the findings of the present invention, a suitable therapy for a subject can be reliably selected. Severe side effects caused by the wrong treatment of patients can be avoided. As described below in detail, therapies for the diseases or disorders accompanied with the cardiac necrosis are different.

It is to be understood that in a preferred embodiment of the method of the present invention, said reference amounts are the upper limits of normal (ULN) for the cardiac troponin and the BNP-type peptide.

In a furthermore preferred embodiment of the method of the present invention, an increased amount of the cardiac troponin and an increased amount of the BNP-type peptide is indicative for a cardiac necrosis caused by initial heart failure.

Also, in a preferred embodiment of the method of the present invention, an increased amount of the cardiac troponin and an amount of the BNP-type peptide being not increased is indicative for cardiac necrosis caused by a coronary heart disease.

The definitions and explanations of the terms given above apply mutatis mutandis for the following methods except specified otherwise below.

The present invention also relates to a method of determining whether a subject suffering from cardiac necrosis is susceptible for a therapy against initial heart failure comprising:
(a) determining the amount of a cardiac troponin and the amount of a BNP-type peptide in a sample of a subject suffering from cardiac necrosis; and
(b) comparing the amount of the cardiac troponin and the amount of said BNP-type peptide to reference amounts, whereby it is to be determined whether the subject is susceptible to a therapy against initial heart failure.

The phrase "determining whether a subject suffering from cardiac necrosis is susceptible for a therapy against initial heart failure" as used herein means assessing whether a subject will be susceptible for a therapy against initial heart failure or not. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools. Further details on said statistical evaluation are to be found elsewhere in this specification.

Figure 1:
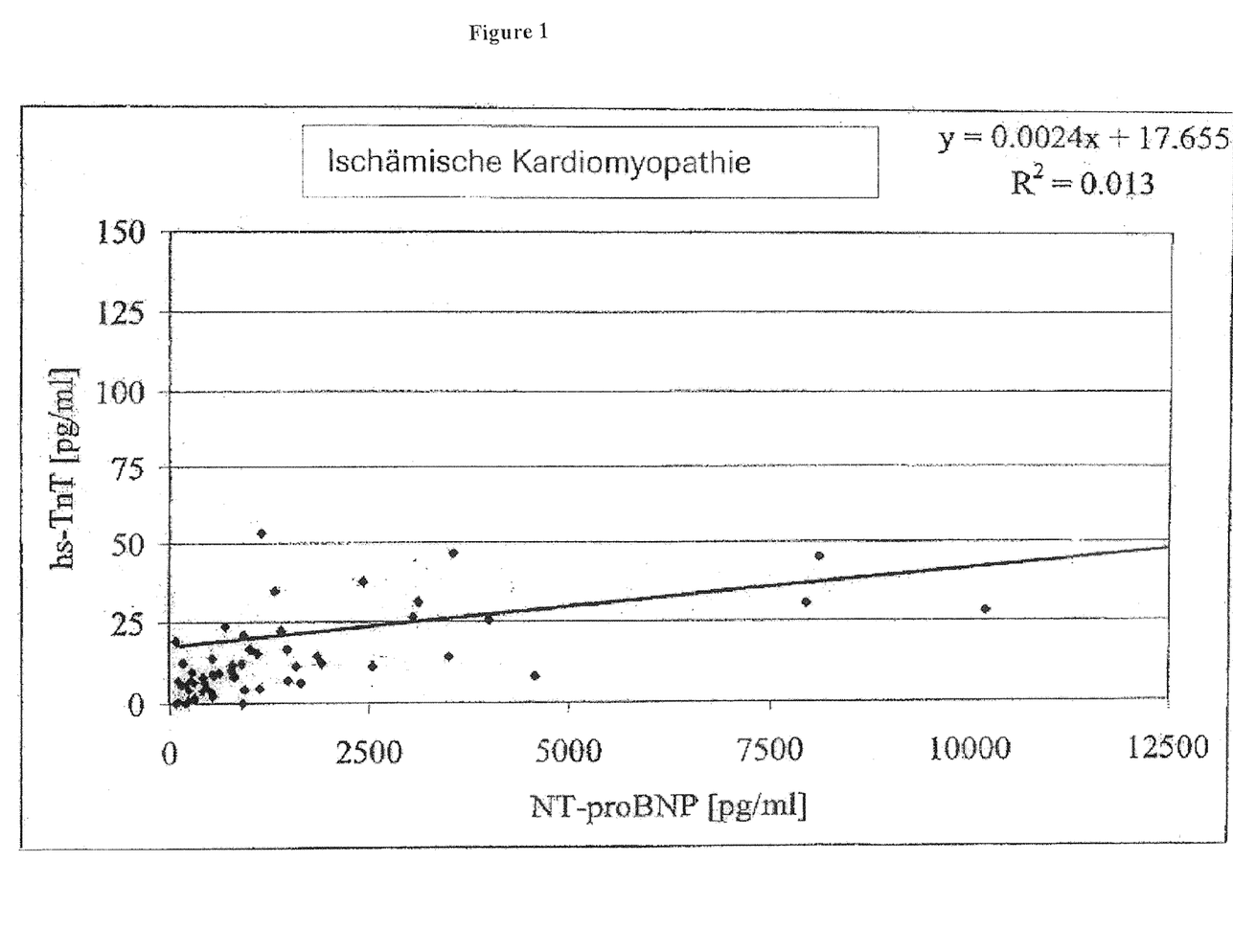
FIG. 1: Linear regression analysis of NT-proBNP and troponin T in patients suffering from ischemic cardiac myopathy.

The term "therapy against initial heart failure" encompasses drug-based as well as other therapies of heart failure. More preferably, said therapy against initial heart failure is selected from the group consisting of: medicament based therapy, preferably, administration of ACE inhibitors, administration of β-blockers, administration of digital AT1 and/or AT2 blockers, administration of inotropic drugs, assist device-based therapies, interventional therapy is cardiac resynchronisation therapy (CRT) or based on implantation of a cardioverter defibrillator (ICD) and heart transplantation. More preferably, the medicament is an ACE inhibitor, preferably captopril, enalapril, fosinopril, lisinopril, perindopril, quinapril, ramipril, or trandolapril, an AT-1 receptor blocking agent, preferably, candesartan, losartan, or valsartan, a β-receptor blocking agent, preferably, bisoprolol, carvedilol, metoprolol or succinate, or an an aldosterone antagonist, preferably, spironolacton or eplerenone. Further details on the therapies will be found in Heart Disease, 2005, 7th Edition, Eds. Braunwald, Elsevier Sounders, see FIG. 24G-1 to 24G-7.

In a preferred embodiment of the method of the aforementioned present invention, said reference amounts are the upper limits of normal (ULN) for the cardiac troponin and the BNP-type peptide.

Furthermore, in a preferred embodiment of the method of the present invention, an increased amount of the cardiac troponin and an increased amount of the BNP-type peptide is indicative for a subject being susceptible for a therapy against initial heart failure.

Moreover, in a preferred embodiment the method of the present invention may further comprise a supplementary diagnostic technique selected from the group consisting of: echocardiography, computed tomography, NMR-based diagnostics, electrocardiography, x-ray diagnostics of the thorax and spirometry. Further details on the therapies will be found in Heart Disease, 2005, 7th Edition, Eds. Braunwald, Elsevier Sounders, see FIG. 24G-1 to 24G-7.

The present invention also encompasses a method for determining whether a subject suffering from cardiac necrosis is susceptible for a therapy against coronary heart disease comprising
(a) determining the amount of cardiac troponin and the amount of a BNP-type peptide in a sample of a subject suffering from cardiac necrosis; and
(b) comparing the amount of the cardiac troponin and the amount of the BNP-type peptide to reference amounts, whereby it is to be determined whether the subject is susceptible to a therapy against coronary heart disease.

The phrase "determining whether a subject suffering from cardiac necrosis is susceptible for a therapy against coronary heart disease" as used herein means assessing whether a subject will be susceptible for a therapy against coronary heart disease or not. As will be understood by those skilled in the art again, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools. Further details on said statistical evaluation are to be found elsewhere in this specification.

The term "therapy against coronary heart disease" encompasses drug-based as well as invasive therapies against a coronary heart disease. More preferably, the therapy against coronary heart disease is selected from the group consisting of: administration of inhibitors of thrombocyte aggregation, preferably, aspirin or clopidogrel, and cardiac interventions. Preferred cardiac interventions in accordance with the present invention are specifically selected from the group consisting of percutaneous coronary angioplasty, percutaneous transluminal coronary balloon angioplasty, laser angioplasty, coronary stent implantation, bypass implantation or intraluminal techniques aiming to restore blood flow, vessel patency, stabilize plaque, and/or reduce intracoronary thrombus load.

In a preferred embodiment of the aforementioned method of the present invention said reference amount are the upper limits of normal (ULN) for the cardiac troponin and the BNP-type peptide.

Moreover, in a preferred embodiment of the method of the present invention, an increased amount of the cardiac troponin and an amount of the BNP-type peptide being not increased as indicative for a subject being susceptible for a therapy against coronary heart disease.

Moreover, in a preferred embodiment the method of the present invention may further comprise a supplementary diagnostic technique selected from the group consisting of: angiography, echocardiography, computer tomography, NMR-based diagnostics, electrocardiography, x-ray diagnostics of the thorax and spirometry.

In principal, the present invention encompasses the use of a cardiac troponin and a BNP-type peptide for the preparation of a diagnostic composition for diagnosing the cause of cardiac necrosis in the subject, for determining whether a subject suffering from cardiac necrosis is susceptible for a therapy against initial heart failure or for determining whether a subject suffering from cardiac necrosis is susceptible for a therapy against coronary heart disease.

Moreover, the present invention also includes a method of monitoring the success of a therapy against coronary heart disease comprising:

(a) determining the amount of a cardiac troponin in at least first and a second sample of a subject subjected to the therapy wherein the first sample has been obtained prior and the second sample has been obtained after the therapy has been started; and (b) comparing the amounts from the first and the second sample, whereby a decreased amount of the cardiac troponin in the second versus the first sample is indicative for the success.

Preferably, a BNP-type peptide is also determined in the first and second sample. A decrease in the amount of the BNP-type peptide will be, furthermore, indicative of success of the applied treatment regimen.

Furthermore, the present invention encompasses a method of monitoring the success of a therapy against initial heart failure comprising:

(a) determining the amount of a cardiac troponin and a BNP-type peptide in at least first and a second sample of a subject subjected to the therapy wherein the first sample has been obtained prior and the second sample has been obtained after the therapy has been started; and (b) comparing the amounts from the first and the second sample, whereby a decreased amount of the cardiac troponin and a decreased amount of the BNP-type peptide in the second versus the first sample is indicative for the success.

The term "monitoring" as used herein relates to keeping track of the effects caused by a treatment regimen to the amounts of NT-proBNP and/or the cardiac troponin. It is to be understood that the amounts must be determined at least prior and after the onset of the treatment regimen. However, the amounts may be determined at other stages, too.

The term "success" as used herein refers to at least an amelioration of the prognosis, symptoms or clinical signs accompanied with the diseases, i.e. coronary heart disease or initial heart failure.

The present invention also relates to a diagnostic device adapted for carrying out any one of the methods of the preset invention comprising means for the determination of the amount of cardiac troponin and the amount of a BNP-type peptide in a sample of a subject suffering from cardiac necrosis and means for preparing the amounts to reference amounts.

The term "device" as used herein relates to a system of means comprising at least the aforementioned means operatively linked to each other as to allow the prediction. Preferred means for determining the amount of a cardiac troponin and a BNP-type peptide as well as means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. The computer unit, preferably, comprises a database including the stored reference amounts or values thereof recited elsewhere in this specification as well as a computer-implemented algorithm for carrying out a comparison of the determined amounts for the polypeptides with the stored reference amounts of the database. Computer-implemented as used herein refers to a computer-readable program code tangibly included into the computer unit. Alternatively, where means such as test strips are used for determining the amount of the peptides or polypeptides, the means for comparison may comprise control strips or tables allocating the determined amount to a reference amount. The test strips are, preferably, coupled to a ligand which specifically binds to the peptides or polypeptides referred to herein. The strip or device, preferably, comprises means for detection of the binding of said peptides or polypeptides to the ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of raw data which need interpretation by the clinician. Preferably, the output of the device is, however, processed, i.e. evaluated, raw data the interpretation of which does not require a clinician. Further preferred devices comprise the analyzing units/devices (e.g., biosensors, arrays, solid supports coupled to ligands specifically recognizing the natriuretic peptide, plasmon surface resonance devices, NMR spectrometers, mass-spectrometers etc.) and/or evaluation units/devices referred to above in accordance with the method of the invention.

Finally, the present invention relates to a diagnostic kit adapted for carrying out any one of the methods of the present invention comprising means for the determination of the amount of a cardiac troponin and the amount of a BNP-type peptide in a sample of a subject suffering from cardiac necrosis and means for comparing the amounts to reference amounts.

The term "kit" as used herein refers to a collection of the aforementioned means, preferably, provided in separately or within a single container. The container, also preferably, comprises instructions for carrying out the method of the present invention.

All references cited in this specification are herewith incorporated by reference with respect to their entire disclosure content and the disclosure content specifically mentioned in this specification.

SPECIFIC EMBODIMENTS

The following Examples shall merely illustrate the invention. They shall not be construed, whatsoever, to limit the scope of the invention.

Example 1

NT-proBNP and Troponin T in Patients with Coronary Heart Disease

NT-proBNP and sensitive troponin T was measured in blood samples of a total of 235 patients suffering from stable coronary heart disease. NT-proBNP was measured using the ELECSYS assay and troponin T was assayed by the sensitive troponin T test purchased from Roche Diagnostics. Patients were subjected to a detailed cardiologic investigation including echocardiography and coronary angioplasty. The coronary heart disease was subclassified into 1-, 2- or 3-vessel diseases, whereby stenosis of more than 50% should occur per vessel.

Figure 2:
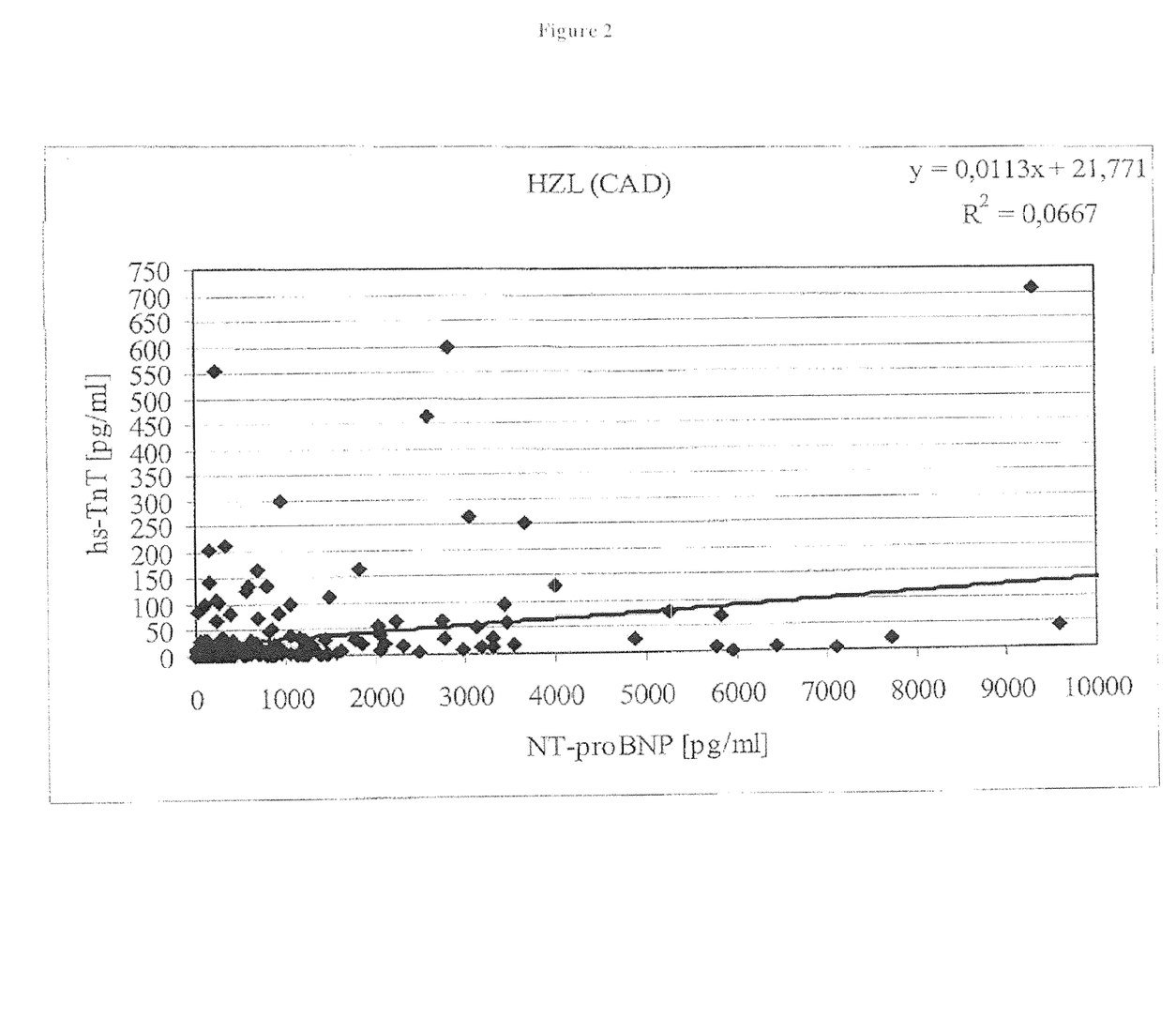
FIG. 2: Linear regression analysis of NT-proBNP and troponin T in patients suffering from coronary heart disease.
Figure 3:
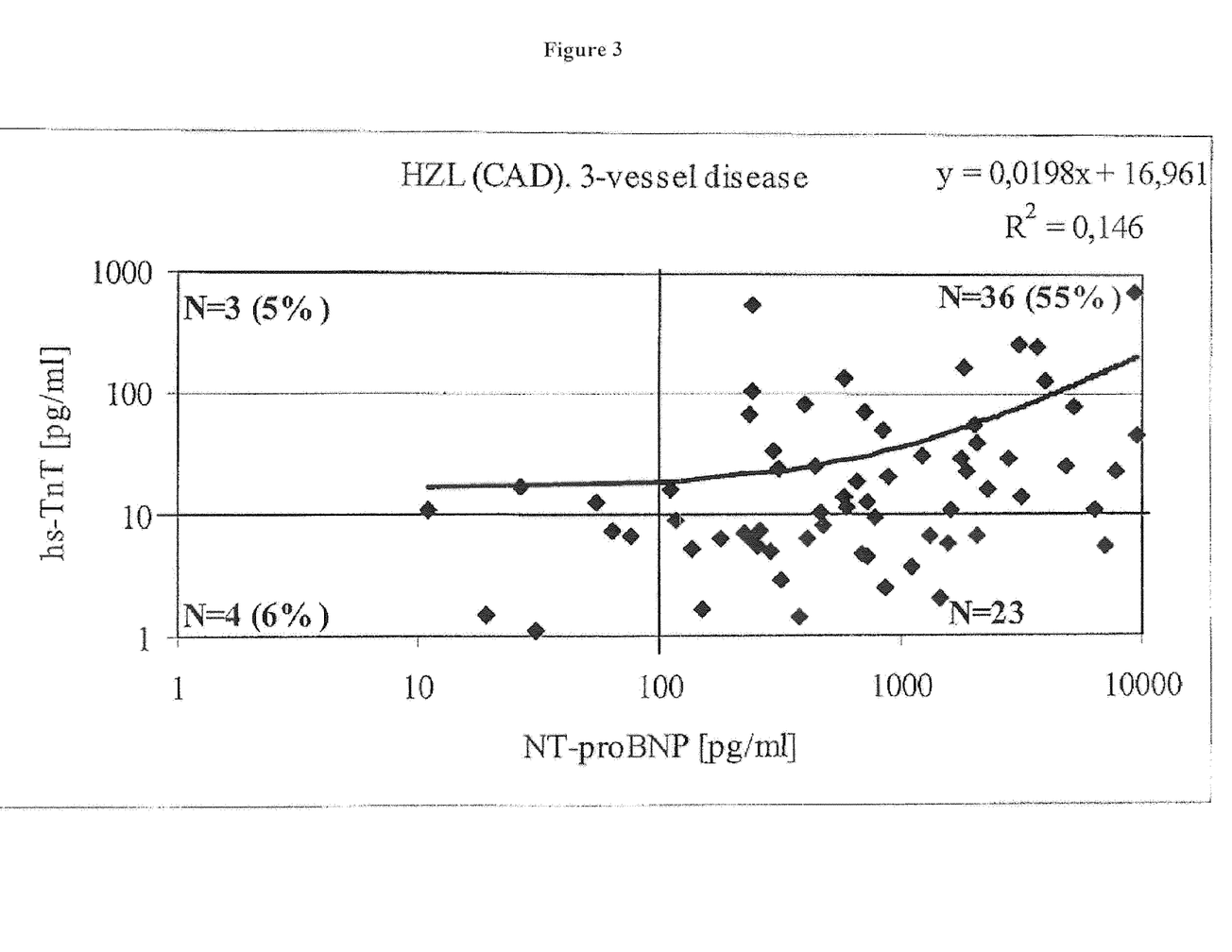
FIG. 3: Linear regression analysis of NT-proBNP and troponin T in a subgroup of patients suffering from 3-vessel disease.

The two biomarkers were analyzed by statistical linear regression analysis. As shown in FIG. 2, a correlation of NT-proBNP and sensitive troponin T was found with a correlation R value of 0.0667. Patients having an increased troponin T level and a normal NT-proBNP exhibited a substantial stenosis when investigated by angiography while patients having an elevated NT-proBNP level and an elevated troponin T showed no such substantial stenosis when investigated by angiography. Similar results were obtained for a subgroup of patients suffering from the 3-vessel disease (see FIG. 3).

Fifty-nine patients exhibiting an ischemic cardiac myopathy were investigated for the biomarkers as described above. Similarly, a correlation between NT-proBNP and troponin T was found at an R value of 0.013 (see FIG. 1).

Example 2

NT-proBNP and Troponin T of Patients Suffering from Cardiac Necrosis as Investigated by Thallium Scintigraphy A total of 143 patients who underwent thallium scintigraphy for suspected significant coronary artery disease were studied.

Patients underwent bicycle exercise testing using a standard exercise protocol or received pharmacological testing with dipyridamol at a dose of 42.72 mg (±7.61) using a standard protocol. Allocation to dynamic or pharmacological exercise testing was left at the discretion of the nuclear cardiologist. The protocol was approved by the local ethical committee of the University of Heidelberg, and all patients gave informed consent prior to inclusion.

Single-photon emission computed tomography myocardial perfusion (SPECT) imaging was carried out as follows: Thallium was administered at peak stress, and imaging was performed immediately thereafter. Four hours later, a repeat imaging was performed. A 17 segment myocardial model was used for semiquantitative analysis. Two nuclear cardiologists unaware of biomarker results categorized the images as having no perfusion defects, only reversible perfusion defects, and fixed perfusion defects. Patients with a combination of reversible, partially reversible, and fixed perfusion defects were excluded from primary analysis and evaluated separately.

Blood samples were obtained immediately before, immediately after, and 4 hours after stress testing. A very late blood sample was collected in all patients with a third scan (redistribution scan) on the next day (n=20). Blood samples were placed on ice and processed within 30 minutes. Plasma aliquots were stored at −80° C. and thawed before analysis.

Statistical analysis was carried out as follows: Plasma concentrations of cardiac troponin T and NT-pro BNP with the corresponding interquartile range or as mean values with the corresponding standard error. The baseline characteristics of patient groups were compared using the Mann-Whitney U test or Student's t-test for continuous variables and the chi-square test for categorical variables. The Kolmogorov-Smirnov test was used to test for normal distribution. For all analyses, a value of P<0.05 was regarded as statistically significant. All statistical analyses were carried out using the SPSS software package version 12.01 (SPSS Inc, Chicago, Ill., USA).

Figure 4:
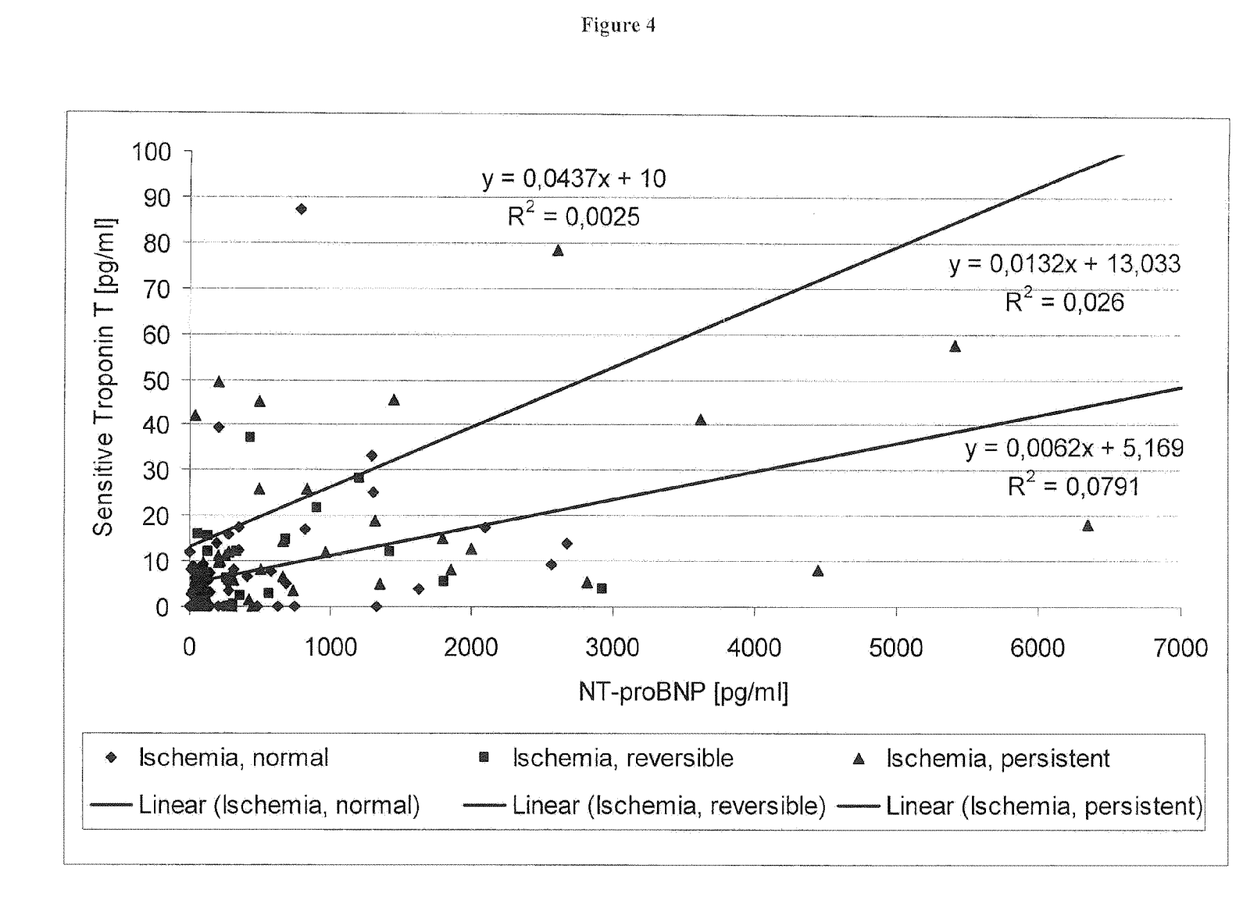
FIG. 4: Linear regression analysis of NT-proBNP and troponin T in patients suffering from cardiac necrosis which have been subjected to physical stress (bicycle exercise) and pharmacological stress. The patients were classified by thallium scintigraphy for three different types of ischemia, i.e. no ischemia (n=62 patients), reversible ischemia (n=24 patients) and persisting ischemia (n=57 patients). Non-ischemic patients showed a weaker correlation (R2=0.0025) of the amounts of NT-proBNP and troponin T than patients with reversible ischemia (R2=0.026). The best correlation could be seen for patients with persisting ischemia (R2=0.0791).

The results are shown in the following table and FIG. 4.

TABLE

Amounts of sensitive troponin T and NT-proBNP in patients classified according to their apparent ischemia in thallium scintigraphy

|  | normal | reversible ischemia | persisting ischemia |
|---|---|---|---|
| NT-proBNP (pg/ml) | 139 | 327 | 535 |
| Troponin T (pg/ml) | 4.75 | 5.85 | 11.19 |

What is claimed is:

1. A method of diagnosing initial heart failure as a cause of cardiac necrosis in a human subject suffering from cardiac necrosis, the method comprising the steps of:
    contacting, in vitro, a portion of a sample from a subject with a ligand comprising specific binding affinity for troponin T;
    contacting, in vitro, a portion of the sample from the subject with a ligand comprising specific binding affinity for NT-pro BNP;
    calculating an amount of the troponin T and an amount of NT proBNP based on said steps of contacting; and
    providing a diagnosis of initial heart failure as the cause of cardiac necrosis if the amount of troponin T is greater than an upper limit of normal for troponin T between 0.001 and 0.01 ng/ml and the amount of NT-proBNP is greater than an upper limit of normal for NT-proBNP between 100 and 150 pg/ml.

2. The method of claim 1 wherein the upper limit of normal for troponin T is 0.001 ng/ml and the upper limit of normal for NT-proBNP is 125 pg/ml.

3. A method of treating a human subject suffering from cardiac necrosis, the method comprising the steps of:
    contacting, in vitro, a portion of a sample from a subject with a ligand comprising specific binding affinity for troponin T;
    contacting, in vitro, a portion of the sample from the subject with a ligand comprising specific binding affinity for NT-pro BNP;
    calculating an amount of the troponin T and an amount of NT proBNP based on said steps of contacting; and
    treating the subject with one of ACE inhibitors, β-blockers, digital AT1 blockers, digital AT2 blockers, inotropic drugs, assist device-based therapies, and heart transplantation if the amount of troponin T is greater than an upper limit of normal for troponin T between 0.001 and 0.01 ng/ml and the amount of NT-proBNP is greater than an upper limit of normal for NT-proBNP between 100 and 150 pg/ml.

4. The method of claim 3 wherein the upper limit of normal for troponin T is 0.001 ng/ml and the upper limit of normal for NT-proBNP is 125 pg/ml.

5. The method of claim 3 wherein said step of treating comprises treating the subject with an ACE inhibitor selected from the group consisting of captopril, enalapril, fosinopril, lisinopril, perindopril, quinapril, ramipril, and trandolapril.

6. A method of treating a human subject suffering from cardiac necrosis, the method comprising the steps of:
    contacting, in vitro, a portion of a sample from a subject with a ligand comprising specific binding affinity for troponin T;

contacting, in vitro, a portion of the sample from the subject with a ligand comprising specific binding affinity for NT-pro BNP;

calculating an amount of the troponin T and an amount of NT proBNP based on said steps of contacting; and treating the subject with one of an inhibitor of thrombocyte aggregation and cardiac intervention if the amount of troponin T is greater than an upper limit of normal for troponin T between 0.001 and 0.01 ng/ml and the amount of NT-proBNP is less than an upper limit of normal for NT-proBNP between 100 and 150 pg/ml.

7. The method of claim 6 wherein the upper limit of normal for troponin T is 0.001 ng/ml and the upper limit of normal for NT-proBNP is 125 pg/ml.

8. The method of claim 6 wherein the step of treating comprises treating the subject with an inhibitor of thrombocyte aggregation selected from the group consisting of aspirin and clopidogrel.

9. A diagnostic kit adapted for carrying out the method of claim 1 comprising means for determination of an amount of troponin T in a sample from a human subject, means for determination of an amount of NT-proBNP in a sample from a human subject, means for comparing the determined amounts to upper limits of normal, and instructions for carrying out the method.

10. The method of claim 1, wherein said step of calculating comprises enzyme-linked immunosorbent assay.

11. The method of claim 1, wherein the sample is selected from the group consisting of blood, plasma, serum, or urine.

12. The method of claim 1, wherein the ligand comprises an antibody.

13. A method of diagnosing coronary heart disease as a cause of cardiac necrosis in a human subject suffering from cardiac necrosis, the method comprising the steps of:

contacting, in vitro, a portion of a sample from a subject with a ligand comprising specific binding affinity for troponin T;

contacting, in vitro, a portion of the sample from the subject with a ligand comprising specific binding affinity for NT-pro BNP;

calculating an amount of the troponin T and an amount of NT proBNP based on said steps of contacting; and providing a diagnosis of coronary heart disease as the cause of cardiac necrosis if the amount of troponin T is greater than an upper limit of normal for troponin T between 0.001 and 0.01 ng/ml and the amount of NT-proBNP is less than an upper limit of normal for NT-proBNP between 100 and 150 pg/ml.

14. The method of claim 13, wherein the upper limit of normal for troponin T is 0.001 ng/ml and the upper limit of normal for NT-proBNP is 100 pg/ml.

15. The method of claim 13, wherein said step of calculating comprises enzyme-linked immunosorbent assay.

16. The method of claim 13, wherein the sample is selected from the group consisting of blood, plasma, serum, or urine.

17. The method of claim 13, wherein the ligand comprises an antibody.

18. A method of selecting a treatment for a subject suffering from cardiac necrosis, the method comprising:

contacting, in vitro, a portion of a sample from a subject with a ligand comprising specific binding affinity for troponin T;

contacting, in vitro, a portion of the sample from the subject with a ligand comprising specific binding affinity for NT-pro BNP;

calculating an amount of the troponin T and an amount of NT proBNP based on said steps of contacting, thereby determining the amount of troponin T is greater than an upper limit of normal for troponin T between 0.001 and 0.01 ng/ml and the amount of NT-proBNP is greater than an upper limit of normal for NT-proBNP between 100 and 150 pg/ml; and selecting a treatment based on said step of calculating, the treatment comprising one of ACE inhibitors, β-blockers, digital AT1 blockers, digital AT2 blockers, inotropic drugs, assist device-based therapies, and heart transplantation.

19. The method of claim 18, wherein the upper limit of normal for troponin is 0.001 ng/ml and the upper limit of normal for NT-proBNP is 125 pg/ml.

20. The method of claim 18 further comprising the step of treating the subject with one of ACE inhibitors, β-blockers, digital AT1 blockers, digital AT2 blockers, inotropic drugs, assist device-based therapies, and heart transplantation.

21. The method of claim 20, wherein said step of treating comprises treating the subject with an ACE inhibitor selected from the group consisting of captopril, enalapril, fosinopril, lisinopril, perindopril, quinapril, ramipril, and trandolapril.

* * * * *